US012171934B2

(12) United States Patent
Trout et al.

(10) Patent No.: US 12,171,934 B2
(45) Date of Patent: Dec. 24, 2024

(54) RESPIRATORY DELIVERY DEVICE

(71) Applicant: De Motu Cordis Pty Ltd, Windsor (AU)

(72) Inventors: Benjamin Barnaby Trout, Brisbane (AU); Lachlan David Farquhar, Brisbane (AU); Patrick Joseph Lynch, Brisbane (AU); John Fredatovich, Brisbane (AU)

(73) Assignee: DE MOTU CORDIS PTY LTD, Windsor (AU)

( * ) Notice: Subject to any disclaimer, the term of this patent is extended or adjusted under 35 U.S.C. 154(b) by 0 days.

(21) Appl. No.: 18/214,915

(22) Filed: Jun. 27, 2023

(65) Prior Publication Data

US 2023/0364362 A1 Nov. 16, 2023

(30) Foreign Application Priority Data

May 23, 2023 (AU) .............................. 2023901616

(51) Int. Cl.
*A61M 15/00* (2006.01)
(52) U.S. Cl.
CPC .... *A61M 15/0035* (2014.02); *A61M 15/0008* (2014.02); *A61M 15/0041* (2014.02); *A61M 2202/064* (2013.01)

(58) Field of Classification Search
CPC .......... A61M 15/0035; A61M 15/0008; A61M 15/0041; A61M 2202/064
See application file for complete search history.

(56) References Cited

U.S. PATENT DOCUMENTS

| 4,423,724 | A  | * | 1/1984 | Young | A61M 15/0033 |
| | | | | | 128/203.15 |
| 2003/0000523 | A1 | * | 1/2003 | Citterio | A61M 15/0028 |
| | | | | | 128/203.15 |
| 2007/0295332 | A1 | * | 12/2007 | Ziegler | A61M 15/0033 |
| | | | | | 128/203.15 |
| 2016/0158470 | A1 | * | 6/2016 | Esteve | A61M 15/0035 |
| | | | | | 128/203.15 |

FOREIGN PATENT DOCUMENTS

WO WO-2020257845 A1 * 12/2020 .......... A61M 11/003

* cited by examiner

*Primary Examiner* — Timothy A Stanis
*Assistant Examiner* — Matthew R Moon
(74) *Attorney, Agent, or Firm* — Hoffmann & Baron, LLP

(57) ABSTRACT

The present disclosure provides for a respiratory delivery device. Particularly, the disclosure provides for a delivery device for use in administering a particulate medicament to a subject's airway and lungs via inhalation. The delivery device may be suitable for emergency medicine for the delivery of active pharmaceutical ingredients including epinephrine.

16 Claims, 7 Drawing Sheets

RESPIRATORY DELIVERY DEVICE

CROSS-REFERENCE TO RELATED APPLICATIONS

This application claims priority to Australian Provisional Patent Application No. 2023901616, filed May 23, 2023, the entire contents of which are incorporated by reference herein.

TECHNICAL FIELD

The present invention relates to a respiratory delivery device. More specifically, the invention relates to a delivery device for use in administering particulate medicament to a subject's airway.

BACKGROUND

For some medical conditions, it can be desirable to administer medicament to a subject via the airways. Inhalers, such as dry powder inhalers (DPIs), can be used for this purpose.

Dry powder inhalers (DPIs) in combination with inhalable dry powders are used in the treatment of diseases such as, respiratory diseases, cardiovascular diseases, diabetes, obesity, and cancer, or symptoms associated with these and other diseases, for example, nausea, vomiting, pain, and inflammation by delivering a consistent dose of a pharmacological agent to the patients' airways through inhalation.

Existing inhalers typically have poor efficiency in regard to delivered dose. This typically restricts the use of inhalers to non-emergency applications wherein reduced dosage is tolerable. Accordingly, new strategies for respiratory administration of medicament would be desirable. It would be particularly desirable to develop new respiratory delivery devices offering improved efficiency in regard to delivered dose.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

In a first aspect, the disclosure resides in a device for delivery of a composition to an airway of a subject, the device having a body defined about a central axis and comprising:
  in fluid communication:
    a composition receptacle adapted to receive a composition capsule containing the composition;
    a dispersion chamber defined by at least one wall which comprises at least one opening therein, the dispersion chamber located substantially adjacent the composition receptacle; and
    a gas outlet,
  wherein the at least one opening is continuous with a flow inlet path extending between the at least one opening and a gas inlet allowing gas to enter the device, the gas inlet formed in the body of the device substantially adjacent the dispersion chamber.

In embodiments, the at least one wall of the dispersion chamber has a distal end adjacent the composition receptacle, defining a first plane, and a proximal end closer to the gas outlet than the distal end and defining a second plane; and the gas inlet is formed in a region of the body of the device overlapping a region formed between the first and second planes.

In embodiments, the flow inlet path extends in a plane substantially perpendicularly to the central axis between the gas inlet and the at least one opening in the at least one wall of the dispersion chamber.

In embodiments, a cross-sectional area of the flow inlet path decreases on moving from the gas inlet in a direction of the at least one opening.

In embodiments, the at least one wall of the dispersion chamber is continuous with a wall at least partially defining the flow inlet path.

In embodiments, the flow inlet path substantially extends between the first and second planes.

In embodiments, the at least one opening in the at least one wall of the dispersion chamber is two openings, each opening having a flow inlet path extending between the opening and the respective gas inlets.

In embodiments, the gas inlets define a gas inlet axis extending between both gas inlets. Preferably, the gas inlet axis extends between the opening of the gas inlets in the body or housing of the device.

In embodiments, each flow inlet path extends at an angle to the gas inlet axis.

In embodiments, each flow inlet path extends at between a 20 to 70 degree angle to the gas inlet axis.

In embodiments, the one or more flow inlet paths each have a point of maximum constriction prior to their associated opening in the at least one wall.

In embodiments, the point of maximum constriction is a constriction in a cross sectional area of the flow inlet path.

In embodiments, the point of maximum constriction is located closer to the respective openings in the at least one wall of the dispersion chamber than to the respective gas inlet.

In embodiments, the point of maximum constriction is located adjacent the respective openings in the at least one wall of the dispersion chamber, optionally wherein the point of maximum constriction is not located immediately adjacent the respective openings in the at least one wall of the dispersion chamber.

In embodiments, the angle of the gas inlet upon entry to the dispersion chamber is between about 25 to about 60 degrees.

In embodiments, the dispersion chamber is adapted to receive the composition for delivery to the subject and to disperse the composition into gas flow between the one or more gas inlets and the gas outlet for delivery to the airway of the subject.

In embodiments, the gas outlet is co-axial with the central axis.

In embodiments, the gas outlet is a mouthpiece.

In embodiments, the dispersion chamber is adapted to promote rotational movement or spinning of the composition capsule within the dispersion chamber.

In embodiments, the dispersion chamber is a vortex chamber.

In embodiments, the device further comprises one or more primers and a cap configured to engage with and displace the one or more primers to pierce the composition capsule upon removal of the cap.

In embodiments, the one or more primers each comprise a cam follower and an associated pin or blade, and wherein the cap comprises one or more cams which are located so as to engage with and displace the respective primer to pierce the composition capsule upon removal of the cap.

In embodiments, the one or more primers is two primers, each of which comprises a cam follower connected to a pin or blade.

In embodiments, the cam followers of the one or more primers prevent the cap from being replaced once removed.

In embodiments, the device further comprises a deagglomerator located substantially adjacent to the dispersion chamber and between the dispersion chamber and the gas outlet.

In embodiments, the deagglomerator is a screen or mesh.

In embodiments, the cap comprises a cap top having one or more elongate members extending from the cap top to the composition receptacle and adapted to hold the composition capsule in place.

In embodiments, the device further comprises a base having a capsule seat adapted to locate the composition capsule in the composition receptacle.

In embodiments, the composition capsule is held in place for piercing by the one or more primers between the capsule seat formed in the base and the one or more elongate members extending from the cap top of the cap.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated that the indefinite articles "a" and "an" are not to be read as singular indefinite articles or as otherwise excluding more than one or more than a single subject to which the indefinite article refers. For example, "a" gas inlet includes one gas inlet, one or more gas inlets or a plurality of gas inlets.

DETAILED DESCRIPTION

Respiratory delivery of therapeutic agents can be suitable for a range of applications. These include applications wherein the subject is typically conscious and responsive, such as administration of powdered epinephrine, vaccines, antibiotics, and insulin.

Without limitation, compositions for delivery referred to herein will typically be in the form of a dry powder. As used herein, and as will be understood by the skilled person, "dry powder" refers generally to a form of particulate medication for respiratory delivery, that is typically delivered, or suitable for delivery, in the absence of propellant.

The composition (e.g. dry powder or particulate medicament) as described herein will suitably comprise at least one "active ingredient", i.e. a component with biological activity. The dry powder or particulate medicament may be in the form of one or more pure, or substantially pure, active ingredients. Alternatively, the dry powder or particulate medicament may include one or more pharmaceutically acceptable components in addition to one or more active ingredients, e.g. fillers, excipients, or diluents, as are well known in the art. For a non-limiting overview of dry powder formulations, the skilled person is directed to Telko and Hickey (2005) 'Dry Powder Inhaler Formulation' Respiratory Care, 50(9), 1209-1227, incorporated herein by reference. It will be appreciated that an active agent and/or a composition containing an active agent may be alternatively referred to as a "drug".

One aspect of the present disclosure provides a device for administering a composition to an airway of a subject. FIGS. 1 to 4E set forth a typical embodiment of a device of this aspect, device 1000. Device 1000 is configured for single-sided operation, i.e. activation by negative pressure as would be achieved by inhalation of a user.

Figure 1:
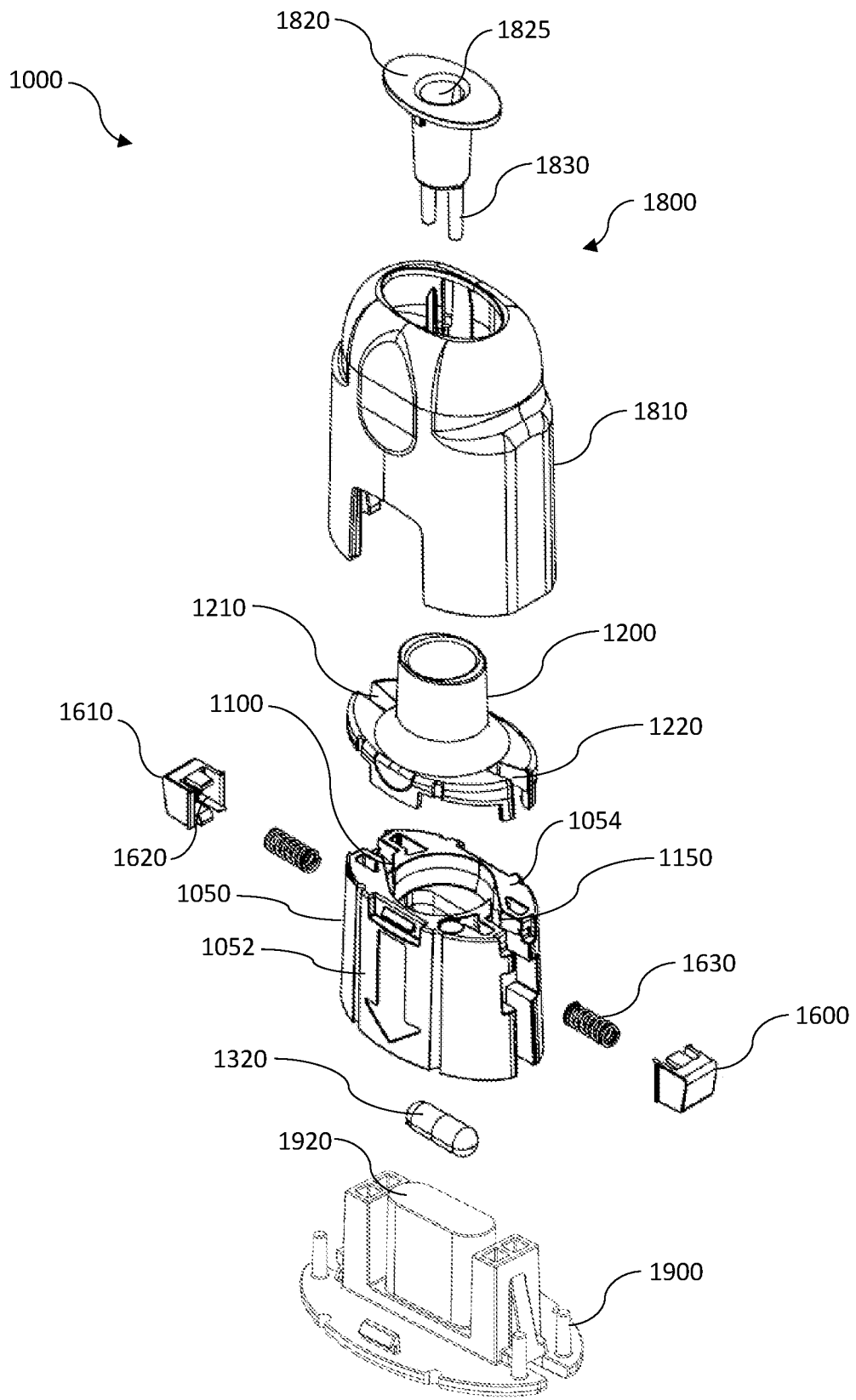
FIG. 1 shows an exploded perspective view of a device according to an embodiment of the present disclosure.

FIG. 1 shows an exploded perspective view of a device 1000 according to an embodiment of the present disclosure, comprising, in part: a body 1050; a first gas inlet 1100; a second gas inlet 1150; an outlet 1200; primers 1600; a cap 1800 having a cap body 1810 and a cap top 1820; and a base 1900.

Figure 2A:
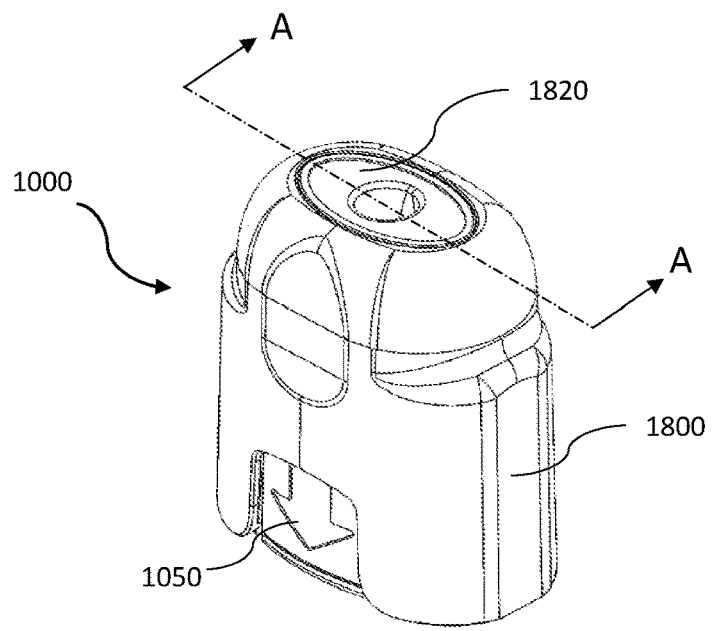
FIG. 2A shows a perspective view of the device of FIG. 1 in a loaded condition.
Figure 2B:
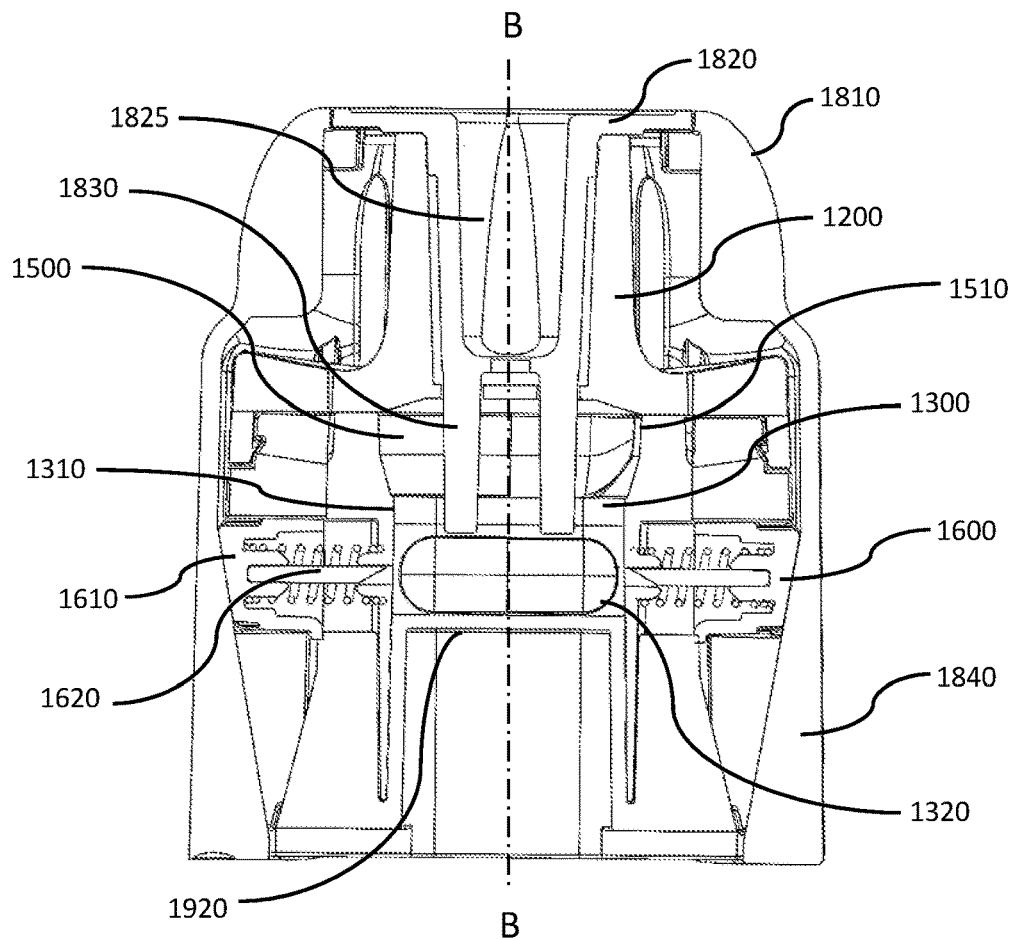
FIG. 2B shows a front cross-sectional view of the device of FIG. 1 in a loaded condition. The cross-sectional view is taken along cross-section A-A shown in FIG. 2A.

FIG. 2A shows a perspective view of the device 1000 of FIG. 1 in a loaded condition; and FIG. 2B shows a front cross-sectional view of the device 1000 of FIG. 1 in a loaded condition, where the cross-sectional view is taken along cross-section A-A shown in FIG. 2A. As depicted in FIG. 2B, the device 1000 is defined about central axis B-B.

Figure 3A:
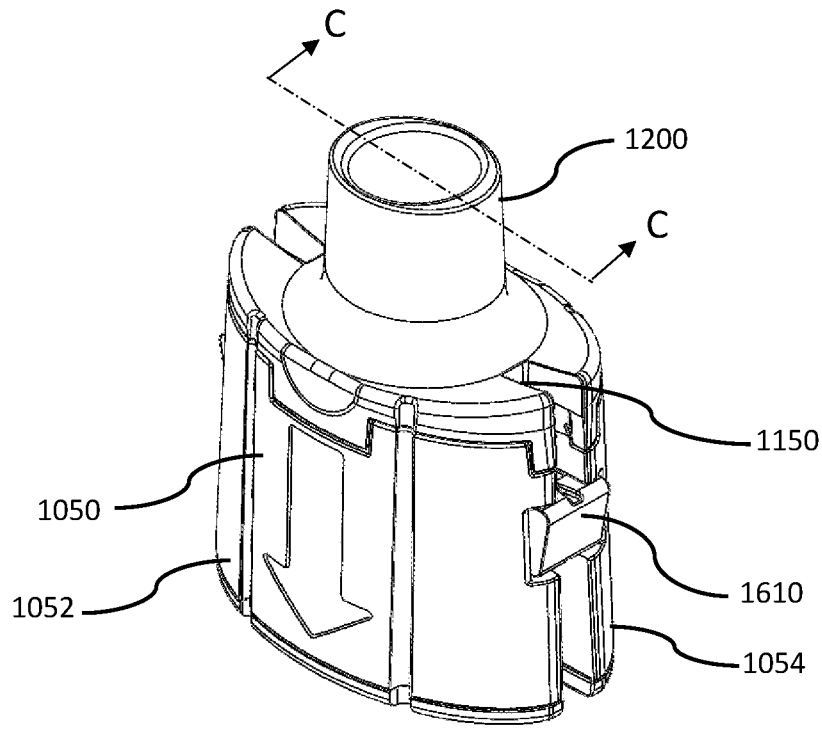
FIG. 3A shows a perspective view of the device of FIG. 1 in an activated state.
Figure 3B:
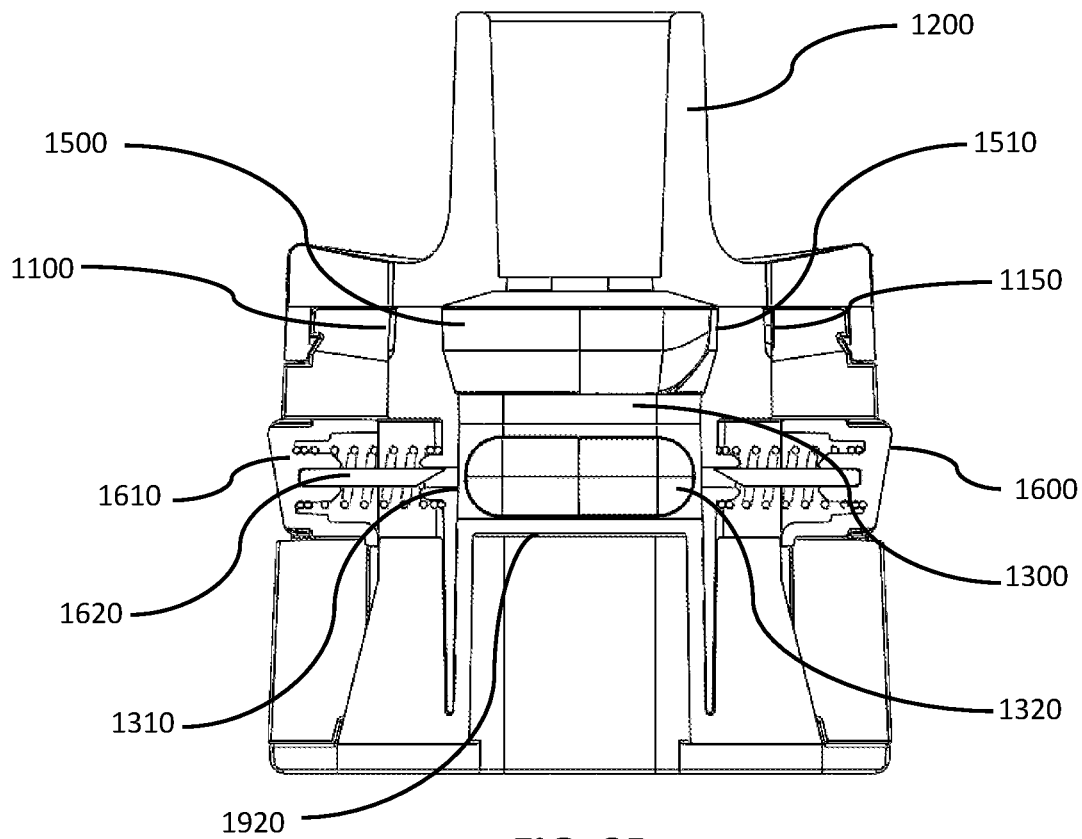
FIG. 3B shows a front cross-sectional view of the device of FIG. 1 in an activated state. The cross-sectional view is taken along cross-section C-C shown in FIG. 3A.
Figure 4A:
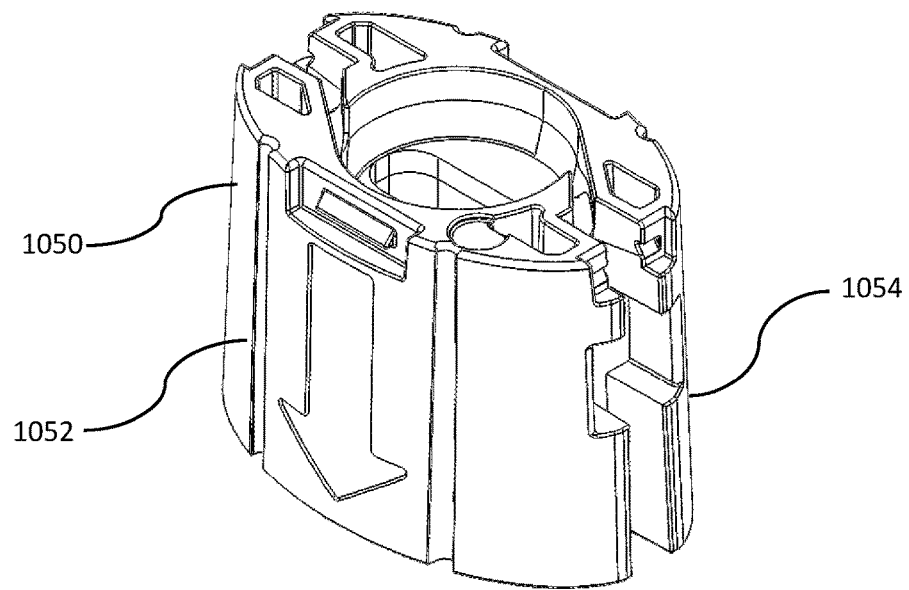
FIG. 4A shows a perspective view of a body of the device of FIG. 1 according to an embodiment of the present disclosure.

As best seen in FIGS. 1 and 4A, the body 1050 comprises a first wall 1052 and a second wall 1054 surrounding a hollow inner region. As best depicted in FIG. 4C, at an outer region of the body 1050, the first and second walls 1052, 1054 are spaced apart, creating a first spaced region 1060 and a second spaced region 1070. The body 1050 is formed from plastic, however, this may be varied as desired. For example, the body 1050 may be metallic, or comprise rubber. Combinations of suitable materials can also be used. FIGS. 3A and 3B show perspective and front cross-sectional views of the device 1000 in an activated state wherein the cap 1800 has been removed. The gas outlet 1200 and the body 1050 are co-axial, being defined about central axis B-B. In this embodiment, the gas outlet 1200 is constructed separately from the body 1050 and a lower portion of the outlet 1200 is configured to connect to the body 1050. Alternatively, the gas outlet 1200 and the body 1050 may be manufactured as a single component.

As shown in FIG. 1, the lower portion of the outlet 1200 is provided with a first cut out 1210 and a second cut out 1220. As best depicted in FIG. 3A, the first and second cut outs 1210, 1220 are continuous with the first and second spaced regions 1060, 1070 of the body 1050. An upper portion of the gas outlet 1200 is generally conical in shape, which can be desirable for use as a mouthpiece. However, the shape of gas outlet 1200 can be varied as desired. Advantageously, the gas outlet 1200 allows for flexibility and versatility in use, with the potential to be used directly as a mouthpiece, or to be used as a connection or fitting for further respiratory equipment.

By way of example, the subject can use the gas outlet 1200 as a mouthpiece, and inhale directly through the gas outlet 1200. Alternatively, the gas outlet 1200 can be used to connect suitable respiratory equipment, such as a mask, inclusive of intraoral masks, oronasal masks, and the like.

Figure 4B:
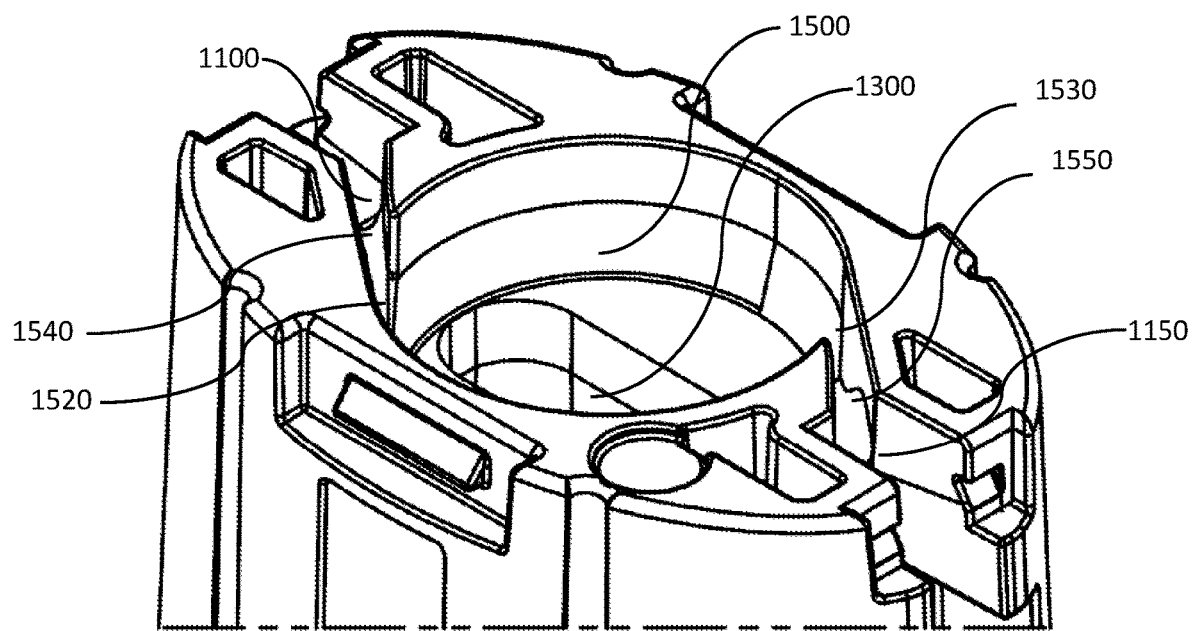
FIG. 4B shows a magnified view of a portion of the perspective view of the body of FIG. 4A.
Figure 4C:
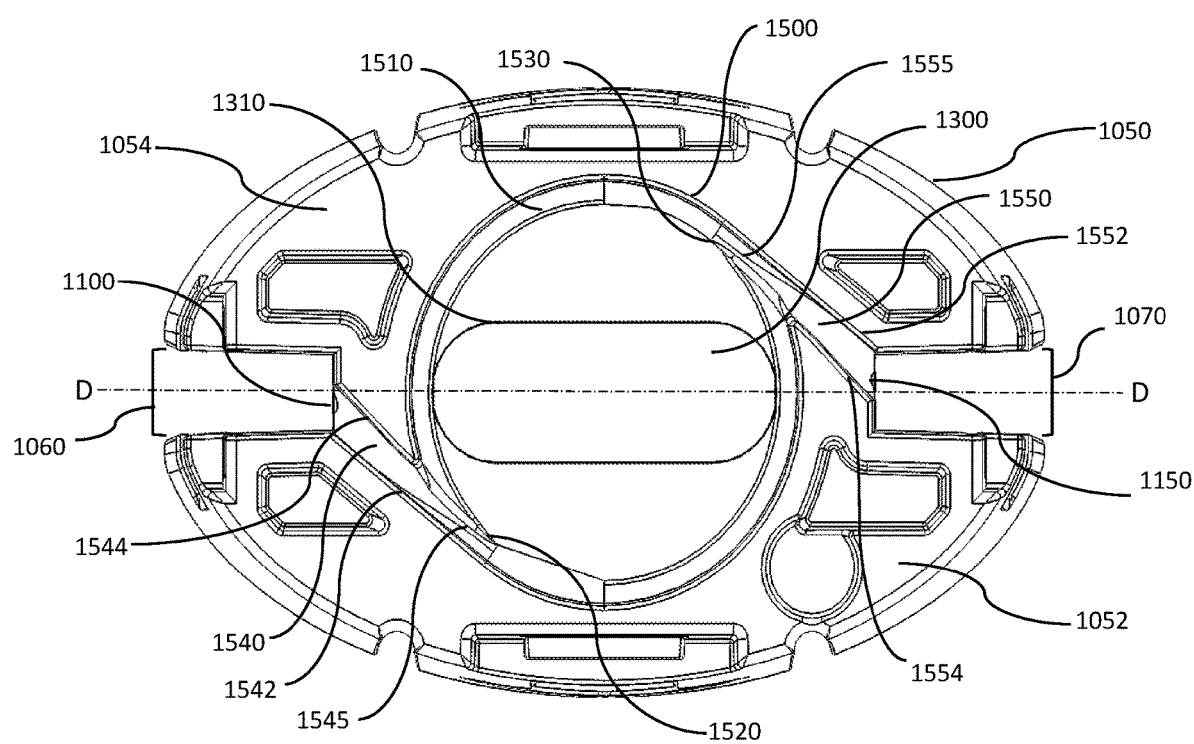
FIG. 4C shows a top view of the body of FIG. 4A.

As best depicted in FIGS. 2B, 4B, and 4C, a composition receptacle 1300 is located within the hollow inner region of the body 1050. The composition receptacle 1300 of the device 1000 is in the form of a well, comprising walls 1310. The composition receptacle 1300 is adapted to fittingly receive a container, such as a composition capsule 1320, comprising a composition to be administered to a subject using the device 1000.

As shown in FIGS. 1, 2B, and 3B, the base 1900 of the device 1000 comprises a capsule seat 1920 that receives the composition capsule 1320 and forms a floor of composition receptacle 1300.

As best shown in FIGS. 2B, 3B, and 4B-4C, a dispersion chamber 1500 is also located within the hollow inner region of the body 1050 of the device 1000. The dispersion chamber 1500 is in the form of a vortex chamber.

The dispersion chamber 1500 is adapted to receive the composition capsule 1320 comprising the composition for delivery to the subject, upon translation of the pierced composition capsule 1320 from the composition receptacle 1300 to the dispersion chamber 1500.

The dispersion chamber 1500 is adapted to promote rotational movement or spinning of the composition capsule 1320 within the dispersion chamber 1500 about, or substantially about, the central axis B-B. The rotational movement or spinning of the composition capsule 1320 within the dispersion chamber 1500 facilitates dispersion of the composition from the composition capsule 1320 and into gas flow between the gas inlets 1100, 1150 and the gas outlet 1200 for delivery to the airway of the subject, via the gas outlet 1200.

As best seen in FIGS. 4B and 4C, the dispersion chamber 1500 is defined by a wall 1510 comprising a first opening 1520 and a second opening 1530 therein. The first and second openings 1520, 1530 are continuous with respective first and second flow inlet paths 1540, 1550 formed at least partially by the body 1050. The first and second flow inlet paths 1540, 1550 extend between the respective first and second openings 1520, 1530 and the respective first and second gas inlets 1100, 1150 also formed at least partially the body 1050 of the device 1000, thereby allowing gas to enter the device 1000. It will be appreciated there may be only one gas inlet, one associated flow inlet path, and one associated opening, but at least two of each are preferred and two may be optimal.

As depicted in FIG. 4C, the first flow inlet path 1540 is at least partially defined between an outer first flow inlet path wall 1542 and an inner first flow inlet path wall 1544; and the second flow inlet path 1550 is at least partially defined between an outer second flow inlet path wall 1552 and an inner second flow inlet path wall 1554.

When the outlet 1200 is connected to the body 1050, the lower portion of the outlet 1200 acts as an upper wall or roof for each of the first and second openings 1520, 1530, the first and second flow inlet paths 1540, 1550, and the first and second gas inlets 1100, 1150.

The wall 1510 of the dispersion chamber 1500 has a distal end adjacent the composition receptacle 1300, defining a first plane, and a proximal end closer to the gas outlet 1200 than the distal end and defining a second plane.

The gas inlets 1100, 1150 are formed at least partially in the body 1050 of the device 1000 substantially adjacent the dispersion chamber 1500. In this embodiment, the gas inlets 1100, 1150 are formed at least partially in a region of the body 1050 of the device 1000 overlapping a region formed between the first and second planes defined by the distal and proximal ends of the wall 1510 of the dispersion chamber 1500.

The first and second flow inlet paths 1540, 1550 extend in a plane substantially perpendicularly to the central axis B-B of the body 1050 between the respective first and second gas inlets 1100, 1150 and the respective first and second openings 1520, 1530.

The flow inlet paths 1540, 1550 substantially extend between the first plane defined at the distal end of the wall 1510 of the dispersion chamber 1500, and the second plane defined at the proximal end of the wall 1510 of the dispersion chamber 1500.

As shown in FIG. 4C, the gas inlets 1100, 1150 define a gas inlet axis D-D extending between the gas inlets 1100, 1150. Each flow inlet path 1540, 1550 extends at an angle to the gas inlet axis D-D. More specifically, each flow inlet path 1540, 1550 extends at between a 20 to 70 degree angle to the gas inlet axis D-D, or at between a 30 to 70 degree angle to the gas inlet axis D-D, or at between a 20 to 60 degree angle to the gas inlet axis D-D, or at between a 30 to 60 degree angle to the gas inlet axis D-D, or at between a 20 to 50 degree angle to the gas inlet axis D-D, or at between a 20 to 50 degree angle to the gas inlet axis D-D. A preferred range may be at between a 30 to 50 degree angle to the gas inlet axis D-D, such as at between a 34 to 48 degree angle to the gas inlet axis D-D.

A cross-sectional area of each of the first and second flow inlet paths 1540, 1550 decreases on moving from the respective first and second gas inlets 1100, 1150 in a direction of the respective first and second openings 1520, 1530. Each flow inlet path 1540, 1550 comprises a point of maximum constriction 1545, 1555 prior to their associated openings 1520, 1530 in the wall 1510 of the dispersion chamber 1500. At the point of maximum constriction 1545, 1555, the cross-sectional area of the respective flow inlet paths 1540, 1550 is at its minimum. The points of maximum constriction 1545, 1555 are located closer to the respective openings 1520, 1530 in the wall 1510 of the dispersion chamber 1500 than to the respective gas inlets 1100, 1150. The points of maximum constriction 1545, 1555 are located substantially adjacent, or substantially immediately adjacent, the respective openings 1520, 1530 in the wall 1510 of the dispersion chamber 1500. In embodiments, the point of maximum constriction 1545, 1555 for each flow inlet path 1540, 1550, is located immediately back from (in a direction toward the gas inlet 110, 1150), or adjacent the point at which the dispersion chamber wall 1510 tapers to a point to provide the respective openings 1520, 1530 in the wall 1510 of the dispersion chamber 1500. The shape of the cross-sectional area of the respective flow inlet paths 1540, 1550 is not limited but may, in an embodiment of the disclosure, be trapezoidal.

As depicted, the device 1000 comprises two primers 1600, flanking the composition receptacle 1300. It will be appreciated, however, that a single primer can also be used.

As best seen in FIG. 2B, the primers 1600 are held within the walls 1051 of the body 1050 in an airtight or substantially airtight manner. The primers 1600 each comprise a button 1610 and a pin 1620. In this embodiment, the buttons 1610 of the respective primers 1600 are loaded with springs 1630. It will be appreciated, however, that other suitable resilient buttons may be used such as, for example, deformable buttons, however this can be varied as desired.

It will be further understood that devices of this aspect, such as device 1000, may comprise a deagglomerator (not shown) adapted to deagglomerate the composition for delivery to the airway of a subject. The deagglomerator may be located adjacent or near to the dispersion chamber 1500.

In one typical embodiment, the deagglomerator is or comprises a screen or mesh comprising a plurality of holes or slots to promote gas turbulence. The screen or mesh deagglomerator may be positioned at a distal end of the outlet 1200, adjacent or near to the dispersion chamber 1500.

Looking at FIG. 2A, there is shown the device 1000 in what may be called a 'closed', 'delivered', 'loaded' or pre-activation state. The cap 1800 is fully down on the body 1050, such that an under surface of the cap 1800, specifically the cap top 1820, is substantially in abutment with an upper surface of the upper portion of the gas outlet 1200. The cap 1800 must be removed from the device 1000 prior to use.

As best depicted in FIGS. 2A and 2B, the cap 1800 comprises a cap body 1810 and a cap top 1820, the cap body 1810 being moveable relative to the cap top 1820 as explained below. A well 1825 is formed in the cap top 1820 and a pair of elongate members 1830 extend from the cap top 1820 to hold the composition capsule 1320 in place, as seen clearly in FIG. 2B. The elongate members 1830 may be in the form of a pair of prongs, as shown. However, the aspects provided herein are not limited to a pair of prongs but there could be 1, 3, 4 or some other number of prongs, or some other structure not in the form of prongs that serves the function of holding the composition capsule 1320 in place in on the capsule seat 1920 of the base 1900 and within the composition receptacle 1300.

The pair of elongate members 1830 extend, in this embodiment, through a deagglomerator (not shown) and so the deagglomerator has two openings formed therein to allow the elongate members 1830 to pass through. The two openings are of a size such that the functionality of deagglomerator is substantially not affected by their presence when the cap top 1820 is removed and elongate members 1830 are no longer present.

The elongate members 1830, when the cap 1800 is fully seated, extend into the dispersion chamber 1500 such that, when the composition capsule 1320 is seated within the composition receptacle 1300, they act to hold the composition capsule 1320 in place. This serves to prevent displacement or movement of the composition capsule 1320 such that it is in an optimal position with respect to the pins 1620 for piercing the composition capsule 1320 upon an initial displacement of the cap body 1810. The composition capsule 1320 will suitably comprise a capsule, such as a HPMC capsule, that can be cut or pierced by pins 1620.

As can be seen in the cross-section of FIG. 2B, the composition capsule 1320 is seated on the capsule seat 1920 and within the composition receptacle 1300. The primers 1600 are in a first retracted position and both the cap body 1810 and the cap top 1820 are in place with the elongate members 1830 of the cap top 1820 holding the composition capsule 1320 in place within the composition receptacle 1300. Even in the retracted position, however, the primers 1600 are tensioned, to a degree, as described below.

A lower portion of the walls of the cap body 1810 have a chamfered or bevelled portion 1840. The buttons 1610 of the primers 1600 are in tensioning contact with an upper region of the chamfered portions 1840 to ensure that even prior to use the primers 1600 are partially pushed into the body of the device. Contact with the chamfered portions 1840 is such that, upon an initial displacement of the cap body 1810 for removal thereof and use of the device 1000, the chamfered portions 1840 further force an increasing amount of displacement, beyond that in the resting or unused state, upon the buttons 1610 thereby forcing the pins 1620 to extend further into the composition receptacle 1300 and pierce the composition capsule 1320 located therein. The displacement of the buttons 1610 may be by the pressure exerted on the resilient material forming the buttons 1610. No separate buttons or switches have to be actioned to release the composition. Instead, the initial displacement of the cap body 1810 automatically results in piercing of the composition capsule 1320 and release of the composition.

During the initial displacement of the cap body 1810 and resulting piercing of the composition capsule 1320, the cap top 1820 has not yet been displaced, remaining in substantial abutment with the upper surface of the outlet 1200. This allows the composition capsule 1320, during piercing, to be held in place within the composition receptacle 1300 by the elongate members 1830 of the cap top 1820 and ensures appropriate and reproducible piercing between multiple devices.

After the composition capsule 1320 has been pierced, further displacement of the cap body 1810 for removal thereof causes the cap body 1810 to engage with a portion of the cap top 1820 such that complete removal of the cap body 1810 also removes the cap top 1820.

Complete removal of the cap 1800 allows for the primers 1600 to retract such that the pins 1620 have retreated from the composition receptacle 1300. Complete removal of the cap 1800 allows for the primers 1600 to retract completely, even beyond that position before cap removal was initiated when they are in tensioning contact with chamfered portions 1840, such that the primers 1600 protrude from the body 1810 of the device 1000. With the primers 1600 protruding from the body 1050 of the device 1000, is not possible to once again simply place the cap 1800 back in full engagement with the device 1000. This is because the chamfered portions 1840 will come into a blocking engagement with an upper surface of the buttons 1610. The angle of the chamfer this time works against the displacement of the buttons 1610 and so the cap 1800 cannot be lowered any further. If a potential user has a device 1000 with the cap 1800 removed, they will immediately know that the device 1000 has been used or that the composition capsule 1320 comprising the composition has otherwise been pierced and is not appropriate for administration. This provides a quick and simple visual queue for a user to know that the device they are carrying or are provided with is fit for purpose. Given the critical nature of the end medical use in many instances, this is an important safety feature.

To further ensure that the cap 1800 cannot be placed back in full engagement with the device 1000 after use of the device 1000, a cantilever system (not shown) is provided within the primers 1600 that, upon complete removal of the cap 1800, is automatically actuated to prevents any further movement of the primer 1800. This ensures that the primers 1800 are locked in their fully retracted position and cannot be displaced inwards allowing the cap 1800 to be replaced.

Complete removal of the cap 1800 permits access to the gas inlets 1100, 1150, and the gas outlet 1200. This may be called the 'open', 'ready', 'enabled' or 'activated' state as device 1000 is ready for use as shown in FIGS. 3A and 3B.

In use, the composition capsule 1320 is translated from inside the composition receptacle 1300 to substantially inside the dispersion chamber 1500 by the gas flow resulting from the application of negative pressure at the gas outlet 1200 by inhalation of the subject.

The composition capsule 1320, which has been displaced substantially into the dispersion chamber 1500, is caused to spin rapidly. In use, the rapid rotation or spinning of the composition capsule 1320 within the dispersion chamber 1500 against or near to the chamber wall 1510 disperses the composition from the composition capsule 1320 through the seal or membrane pierced or cut by the actioning of the primers 1600 during removal of the cap 1800 The composition will be released at this stage due to the gas flow, turbulence and centrifugal force.

More particularly, in use, flow of gas between gas inlets 1100, 1150 and the gas outlet 1200 enters the dispersion chamber 1500 through the respective flow inlet paths 1540, 1550 and the respective openings 1520, 1530, creating a vortex and causing the composition capsule 1320 to rotate within the dispersion chamber 1500.

As best depicted in FIG. 4C, the wall 1510 of the dispersion chamber 1500 is continuous with the outer first flow inlet path wall 1542 and the outer second flow inlet path wall 1552, which at least partially define the respective first and second flow inlet paths 1540, 1550. This configuration forces entering gas flow into a substantially circular, circulating or vortex pathway tangential to or substantially continuous with the wall 1510 of the dispersion chamber 1500. This vortex pathway facilitates dispersion and/or deagglomeration of the composition into gas flow.

Figure 4D:
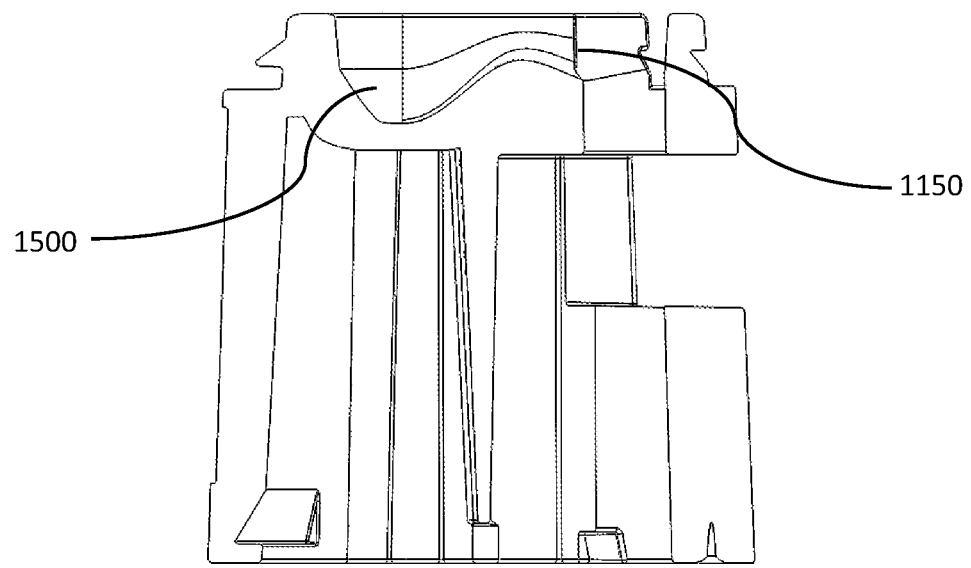
FIG. 4D shows a cross-sectional view of the body of the device of FIG. 4A.
Figure 4E:
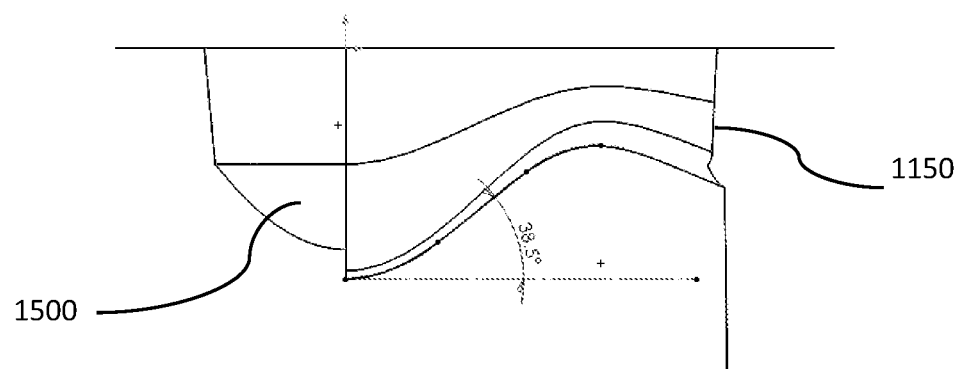
FIG. 4E is an enlarged view of the upper portion of FIG. 4D showing the sloping of a gas inlet into the dispersion chamber.

Further, the gradient of slope of the gas inlets 1100, 1150, as they enter the dispersion chamber 1500 can provide for advantages in terms of air movement into the dispersion chamber 1500 and the subsequent vortex effect generated. This slope can best be seen in FIGS. 4D and 4E. FIG. 4E shows the gas inlet 1150 entering into the dispersion chamber 1500 and indicates the slope of the gas inlet 1150 in doing so. FIG. 4E is an enlarged view of the upper portion of FIG. 4D showing the sloping of the gas inlet 1150 into the dispersion chamber 1500 and showing an indicative angle for the slope of 38.5 degrees. FIG. 4E therefore indicates the manner in which the relevant angle may be measured. It will be appreciated that the angle may vary depending on the point at which it is measured and so, for reference, the angle as discussed here is measured at its steepest point of entry of the gas inlet into the dispersion chamber 1500. In embodiments, this entry angle of the gas inlet (relevant for both gas inlets 1100 and 1150) may be between about 25 to about 60 degrees, or between about 25 to about 50 degrees, or between about 25 to about 45 degrees, or between about 30 to about 60 degrees, or between about 30 to about 50 degrees, or between about 30 to about 45 degrees.

Testing was conducted using a Spraytec® (Malvern Instruments, Worcestershire, UK) to determine the Emitted Dose (ED) and Fine Particle Fraction (FPF) achieved by the present device 1000. The system being addressed during this testing is the inlet geometry and the resulting performance of the device when using a capsule filled with 25 mg of Lactohale 300 Batch:37136. The main results of the testing are summarised below in Table 1.

TABLE 1

Summary of Spraytec ® sample testing results.

| Test Result parameter | Performance of Device 1000 |
|---|---|
| Test Flow Rate (L/Min) | 57.4 |
| Test Pressure (kPa) | 4.02 |
| Mean Mass Emitted from Device(mg) | 17.2 |
| Mean Mass Remaining in Device (mg) | 7.2 |
| Mean Peak FPF (% < 5 μm) | 26.17 |
| Mean FPF (% < 5 μm) | 27.21 |
| % of lactose emitted from capsule | 98.99% |
| % of lactose remaining in device | 29.1% |

The two calculated results were the percentage of lactose emitted from the capsule and the percentage of lactose remaining in the device. These were calculated using the following formulas:

$$\% \text{ Lactose emitted from capsule} = \frac{Mcp - Mca}{Mcp - Mcn} * 100\%$$

Mcp=Mass of capsule prior to testing,
Mca=Mass of capsule after testing,
Mcn=Nominal Mass of unfilled capsule.

$$\% \text{ Lactose remaining in device} = \frac{Mcp - Mca - (Mfp - Mfa)}{Mcp - Mcn} * 100\%$$

Mcp=Mass of capsule prior to testing,
Mca=Mass of capsule after testing,
Mcn=Nominal Mass of unfilled capsule,
Mfp=Mass of full assembly prior to test,
Mfa=Mass of full assembly after testing.

The above testing was also performed on the RS01 inhaler, which is the industry standard inhaler for DPIs, produced and owned by Berry Global Inc and commercially available. While there are several variations of the RS01, testing was performed on the High Resistance RS01, as it allows a narrower range of flow rates to be achieved by the end user, and so is less influenced by the end users lung capacity due to its restrictive nature.

Results showed that the present device 1000 performed better than the RS01, achieving a higher percentage of lactose that made it through to be analysed by the Spraytec®, below 5 μm at 27.21%. Previous testing with an RS01 and 50 mg Lactohale capsules had yielded much lower FPF at just 13.16% on average. The RS01 also had results showing that the amount of Lactohale remaining in the device was far higher (33.4%) than what was seen from testing of the present device 1000. This means that the present device 1000 has on average, more lactose being output at below 5 μm. This indicates that the present device 1000 provides significant advantages as the lower flow rate of 57.4 L/Min is able to be used by a wider range of people.

The conclusions of this testing were that the present device 1000 performed well with a relatively low amount of build-up inside the device in comparison to the RS01. The present device 1000 was able to consistently achieve a higher FPF than the RS01.

Further testing between the present device 1000 and the High Resistance RS01 was performed using a Next Generation Impactor (NGI) testing system. Specifically, the NGI testing system determined, for each of the present device 1000 and the High Resistance RS01, the Aerodynamic Particle Size Distribution (APSD) of an epinephrine and lactose formulation at a strength of 5.2% (1.3 mg epinephrine per 25 mg capsule). The results of the NGI testing are shown in the following two tables (table 2 showing the High Resistance RS01 data and table 3 showing data from the present device, respectively).

TABLE 2

NGI Results for High Resistance RS01
Post Filling High Res RS01
Results mg

| Stage | NGI 1 | NGI 2 | NGI 3 | NGI 4 | NGI 5 | NGI 6 | NGI 7 | NGI 8 | NGI 9 | NGI 10 | NGI 11 | NGI 12 | Mean |
|---|---|---|---|---|---|---|---|---|---|---|---|---|---|
| Throat & Mouth | 0.1925 | 0.1793 | 0.2183 | 0.1870 | 0.1553 | 0.1920 | 0.1309 | 0.1781 | 0.1667 | 0.1777 | 0.1727 | 0.1755 | 0.18 |
| Presep | 0.2923 | 0.2930 | 0.2256 | 0.3146 | 0.2968 | 0.2495 | 0.2843 | 0.4110 | 0.3417 | 0.2803 | 0.2647 | 0.2726 | 0.29 |
| Stage 1 | 0.0146 | 0.0134 | 0.0125 | 0.0148 | 0.0140 | 0.0134 | 0.0133 | 0.0197 | 0.0152 | 0.0125 | 0.0123 | 0.0135 | 0.01 |
| Stage 2 | 0.0572 | 0.0504 | 0.0460 | 0.0537 | 0.0479 | 0.0512 | 0.0425 | 0.0606 | 0.0464 | 0.0474 | 0.0419 | 0.0473 | 0.05 |
| Stage 3 | 0.1363 | 0.1286 | 0.1168 | 0.1229 | 0.3089 | 0.1215 | 0.1141 | 0.1204 | 0.1159 | 0.1195 | 0.1225 | 0.1293 | 0.12 |
| Stage 4 | 0.1243 | 0.1297 | 0.3155 | 0.1154 | 0.0994 | 0.1132 | 0.1161 | 0.1075 | 0.1153 | 0.1231 | 0.1234 | 0.1270 | 0.12 |
| Stage 5 | 0.0444 | 0.0494 | 0.0431 | 0.0420 | 0.0360 | 0.0422 | 0.0421 | 0.0424 | 0.0433 | 0.0467 | 0.0502 | 0.0462 | 0.04 |
| Stage 6 | 0.0174 | 0.0171 | 0.0159 | 0.0165 | 0.0147 | 0.0167 | 0.0169 | 0.0147 | 0.0171 | 0.0171 | 0.0162 | 0.0169 | 0.02 |
| Stage 7 | 0.0084 | 0.0080 | 0.0077 | 0.0070 | 0.0066 | 0.0081 | 0.0084 | 0.0061 | 0.0082 | 0.0081 | 0.0073 | 0.0077 | 0.01 |
| Stage 8 | 0.0047 | 0.0044 | 0.0037 | 0.0039 | 0.0034 | 0.0036 | 0.0045 | 0.0031 | 0.0040 | 0.0040 | 0.0038 | 0.0042 | 0.00 |
| Sum | 0.8921 | 0.8670 | 0.8050 | 0.8780 | 0.7831 | 0.8114 | 0.7730 | 0.9635 | 0.8737 | 0.8364 | 0.8150 | 0.8401 | 0.84 |
| Capsule | 0.2511 | 0.2900 | 0.2786 | 0.2601 | 0.2747 | 0.2931 | 0.2662 | 0.2390 | 0.2810 | 0.2610 | 0.2701 | 0.2827 | 0.27 |
| Device | 0.1397 | 0.1664 | 0.1639 | 0.1571 | 0.1756 | 0.1534 | 0.1628 | 0.1397 | 0.2059 | 0.1437 | 0.1816 | 0.1726 | 0.16 |
| Shot weight (mg) | 23.7 | 24.0 | 23.6 | 23.6 | 23.6 | 23.6 | 23.4 | 23.3 | 23.2 | 23.8 | 24.0 | 24.0 | 23.6 |
| FPD ≤5 μm (mg) | 0.3573 | 0.3504 | 0.3202 | 0.3280 | 0.2868 | 0.3251 | 0.3171 | 0.3153 | 0.3201 | 0.3360 | 0.3388 | 0.3482 | 0.33 |
| FPF (FPD as % total dose) ≤5 μm | 40.0565 | 40.4173 | 39.7787 | 37.3549 | 36.6305 | 40.0677 | 41.0241 | 32.7275 | 36.6365 | 40.1719 | 41.5686 | 41.4462 | 38.99 |
| MMAD (μm) | 2.7431 | 2.6507 | 2.6471 | 2.7336 | 2.7594 | 2.7086 | 2.6292 | 2.8521 | 2.5672 | 2.6204 | 5.5945 | 2.6592 | 2.94 |
| GSD | 1.6345 | 1.6232 | 1.6282 | 1.6657 | 1.6747 | 1.6435 | 1.6297 | 1.7491 | 1.6640 | 1.6392 | 1.6084 | 1.6033 | 1.65 |

TABLE 3

NGI Results for Present Embodiment
Present Embodiment
Results mg

| Stage | NGI 1 | NGI 2 | NGI 3 | NGI 4 | NGI 5 | NGI 6 | NGI 7 | NGI 8 | NGI 9 | NGI 10 | Mean |
|---|---|---|---|---|---|---|---|---|---|---|---|
| Throat & Mouth | 0.0873 | 0.0899 | 0.0907 | 0.1048 | 0.0891 | 0.1159 | 0.0917 | 0.0917 | 0.0926 | 0.1140 | 0.10 |
| Presep | 0.2576 | 0.2592 | 0.2527 | 0.2733 | 0.2257 | 0.2645 | 0.2148 | 0.2550 | 0.2309 | 0.2821 | 0.25 |
| Stage 1 | 0.0144 | 0.0145 | 0.0164 | 0.0158 | 0.0155 | 0.0174 | 0.0162 | 0.0198 | 0.0160 | 0.0161 | 0.02 |
| Stage 2 | 0.0535 | 0.0518 | 0.0550 | 0.0554 | 0.0546 | 0.0645 | 0.0596 | 0.0730 | 0.0635 | 0.0639 | 0.06 |
| Stage 3 | 0.1608 | 0.1582 | 0.1664 | 0.0881 | 0.0709 | 0.1700 | 0.1785 | 0.1971 | 0.1916 | 0.1686 | 0.17 |
| Stage 4 | 0.1628 | 0.1703 | 0.1841 | 0.1913 | 0.1864 | 0.1776 | 0.1949 | 0.2015 | 0.2066 | 0.1626 | 0.18 |
| Stage 5 | 0.0576 | 0.0578 | 0.0729 | 0.0716 | 0.0709 | 0.0603 | 0.0720 | 0.0703 | 0.0738 | 0.0634 | 0.07 |
| Stage 6 | 0.0193 | 0.0183 | 0.0199 | 0.0238 | 0.0242 | 0.0206 | 0.0224 | 0.0218 | 0.0251 | 0.0212 | 0.02 |
| Stage 7 | 0.0080 | 0.0082 | 0.0076 | 0.0104 | 0.0110 | 0.0096 | 0.0119 | 0.0101 | 0.0110 | 0.0087 | 0.01 |
| Stage 8 | 0.0039 | 0.0051 | 0.0048 | 0.0075 | 0.0058 | 0.0061 | 0.0055 | 0.0069 | 0.0060 | 0.0051 | 0.01 |
| Sum | 0.8251 | 0.8332 | 0.8704 | 0.9521 | 0.8538 | 0.9065 | 0.8675 | 0.9471 | 0.9169 | 0.9058 | 0.89 |
| Capsule | 0.2470 | 0.2583 | 0.2723 | 0.2352 | 0.2752 | 0.2711 | 0.2738 | 0.2393 | 0.2407 | 0.2561 | 0.26 |
| Device | 0.2365 | 0.1223 | 0.1440 | 0.1299 | 0.1320 | 0.1304 | 0.1436 | 0.1234 | 0.1248 | 0.1332 | 0.13 |
| Shot weight (mg) | 23.8 | 24.3 | 24.0 | 23.9 | 23.2 | 24.5 | 24.0 | 24.4 | 25.2 | 23.6 | 24.1 |
| FPD ≤5 μm (mg) | 0.4281 | 0.4327 | 0.4722 | 0.5133 | 0.4853 | 0.4639 | 0.5035 | 0.5298 | 0.5336 | 0.4500 | 0.48 |
| FPF (FPD as % total dose) ≤5 μm | 51.8814 | 51.9326 | 54.2540 | 53.9149 | 56.8364 | 51.1707 | 58.0358 | 55.9388 | 58.1943 | 49.6773 | 54.18 |
| MMAD (μm) | 2.7234 | 2.6833 | 2.6151 | 2.6762 | 2.5986 | 2.7352 | 2.6219 | 2.7325 | 2.6392 | 2.7261 | 2.67 |
| GSD | 1.5803 | 1.5907 | 1.6131 | 1.5974 | 1.6082 | 1.6188 | 1.6082 | 1.6055 | 1.5969 | 1.1044 | 1.60 |
| Flow Rate | 60.3 | 60.1 | 61.0 | 51.0 | 60.8 | 61.0 | 61.0 | 60.9 | 60.8 | 61.5 | |
| P2/P3 | 0.2 | 0.2 | 0.2 | 0.2 | 0.2 | 0.3 | 0.3 | 0.3 | 0.3 | 0.2 | |
| Trey MSL | 3648 | 778 | 2893 | 3618 | 3648 | 778 | 8288 | 2107 | 3908 | 2893 | |
| Throat MSL | 832 | 1916 | 3616 | 1916 | 842 | 3616 | 2130 | 2128 | 2123 | 2123 | |
| Presep MSL | 2875 | 1129 | 1207 | 2875 | 1207 | 1229 | 2876 | 2121 | 1298 | 2121 | |
| NGI Body MSL | 1114 | 1114 | 1114 | 1114 | 1114 | 1114 | 1114 | 1114 | 1114 | 1114 | |

Figure 5:
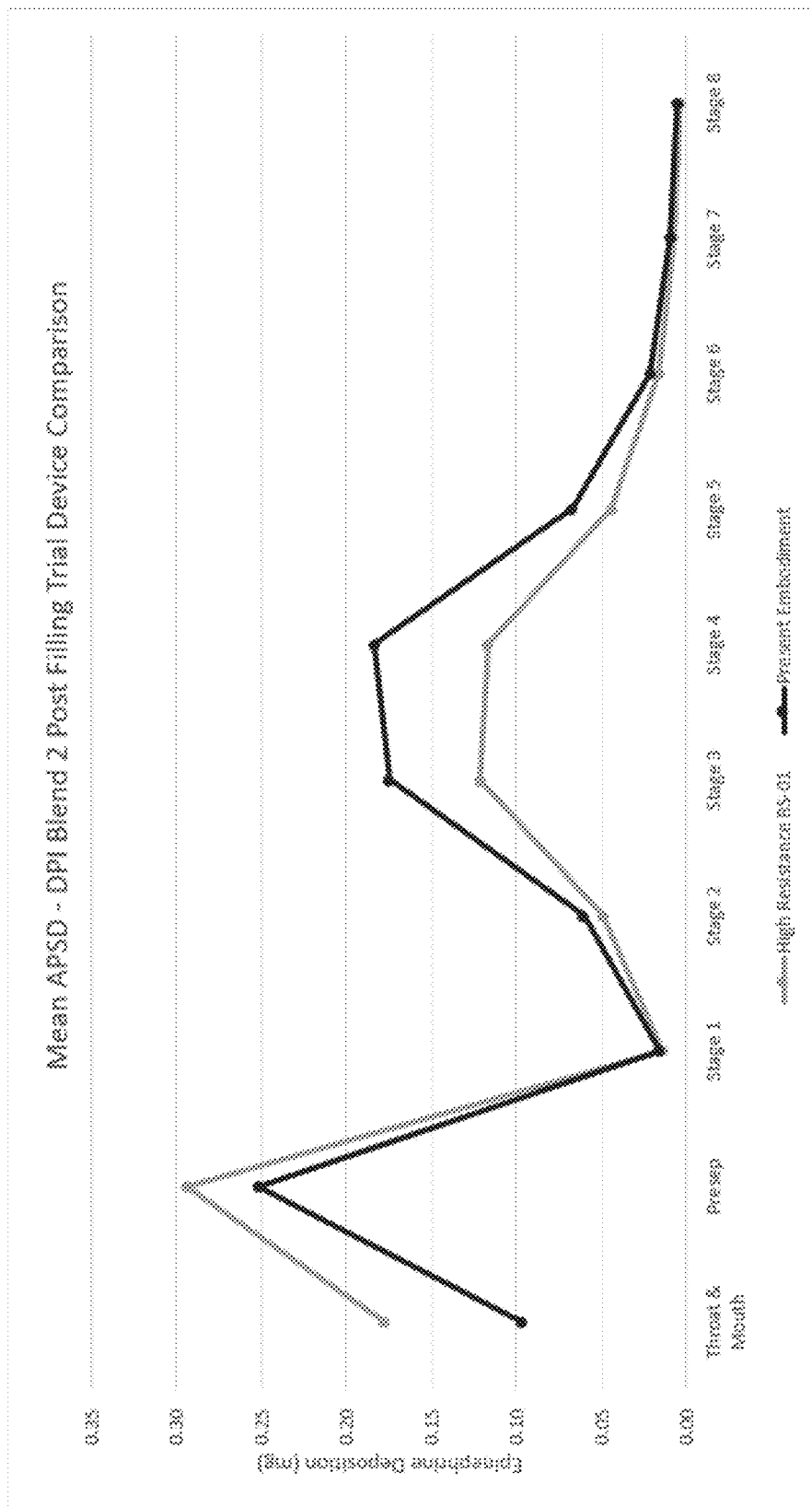
FIG. 5 is a graphical representation of delivery of particulate using the present device and a standard RS01 comparator.

FIG. 5 is a graphical representation of delivery of particulate using the present device and the High Resistance RS01 comparator and also shows the advantages of the present device 1000. The delivery of particulate represented in FIG. 5 is obtained based on the mean ASPD results of the NGI testing as shown in Tables 2 and 3 above. It is apparent from FIG. 5 that the present device 1000 delivers a significantly higher proportion of particles into stages 3 to 5 of the NGI testing system. This indicates a greater delivery of particles of an appropriate size to the deep lung of a user thereby ensuring faster and more complete therapeutic activity.

In use, the composition dispersed by the dispersion chamber 1500 may be further dispersed and/or deagglomerated by the deagglomerator by flow of gas between the gas inlets 1100, 1150 and the gas outlet 1200.

In typical embodiments, wherein the deagglomerator comprises a screen or mesh comprising a plurality of holes or slots to promote gas turbulence, passage of the composition entrained in gas flow through or past the screen or mesh facilitates further dispersion and/or deagglomeration of the composition by resulting gas turbulence.

In use, composition dispersed by gas flow between the gas inlets 1100, 1150 and the gas outlet 1200 through or past dispersion chamber 1500 and, optionally, a deagglomerator of the device 1000, is delivered entrained in the gas flow to the subject's airway, resulting from inhalation by the subject through the gas outlet 1200.

It will be appreciated that devices of the disclosure, such as device 1000, can provide for several important advantages. Particularly, air flow resistance can be tuned to be optimal for specified conditions. Device 1000 is designed such as to provide high resistance thereby allowing for consistent use across consumers with varying lung functions, i.e. it is suitable for users with both strong lung function as well as those having compromised lung function. Device 1000 may provide for improved efficiency of delivery over prior art DPIs such as an RS01 DPI.

Advantageously, embodiments of devices of this aspect, such as device 1000 can be adjusted or modified to alter dosage in accordance with the subject's particular requirements.

For example, the size, shape and/or number of pins 1620 of the primers 1600 can be altered or modified to adjust the rate of delivery of the composition. It will be readily appreciated that a greater number or size of pins 1620 will typically allow for a higher rate of release of the composition from the dispersion chamber 1500, and subsequent delivery to the subject.

Similarly, in embodiments of the device comprising a deagglomerator, characteristics of the deagglomerator (e.g. in respect of the screen properties) can be modified or adjusted to adjust the rate of composition delivery.

Advantageously, embodiments such as device 1000 are typically reliable in use in respect of delivery from containers or capsules.

Additionally, embodiments such as device 1000, particularly wherein the composition receptacle 1300 is formed to fittingly receive the container or composition capsule 1320, can typically be primed and used when positioned in any orientation, with limited or no change in performance.

Advantageously, as hereinabove described, embodiments such as device 1000 typically feature a substantially sealed gas flow path through body 1050 from the inlets 1100, 1150 to the outlet 1200. It will be appreciated that such a sealed flow path substantially prevents, or at least constrains, unwanted escape or leakage of the composition.

Further, device 1000 provides distinct advantages in easy priming of the device 1000 for use simply by removal of the cap 1800 and prevents cap 1800 replacement following use to indicate the capsule containing composition has been pierced and so the device 1000 is no longer fit for further use.

The above is a non-limiting listing of some typical advantages of exemplary embodiments.

As will be readily appreciated by the skilled person, according to these aspects, a suitable composition can be selected for administration to a particular subject, including for a particular therapeutic purpose in relation to a particular condition.

Generally, compositions administered as described herein may include any suitable medicament for administering to the subject's airway, in accordance with the subject's condition and medical requirements. As hereinabove described, typically the composition will be a dry powder, and may be in the form of one or more pure, or substantially pure, active ingredients. The composition may alternatively include one or more pharmaceutically acceptable components in addition to one or more active ingredients, e.g. fillers, excipients, or diluents, as are well known in the art.

As will be appreciated by the skilled person, the size of particles of a dry powder composition administered to a subject's airways can affect the therapeutic efficacy of the dry powder. Typically, the administered microparticles will have a d50 or Mean Mass Aerodynamic Diameter (MMAD) less than 6 µm. As will be understood by the skilled person "d50" or "D50" refers to the value that the particle diameter of 50% by mass of a particulate sample is less than. The d50 particle MMAD is preferably between about 0.5 and about 20 μm, including about: 1, 2, 3, 4, 5, 6, 7, 8, 9, 10, 11, 12, 13, 14, 15, 16, 17, 18, and 19 μm, more preferably between about 0.5 and 10 μm, and even more preferably between 1 and 6 μm, still more preferably between about 2 and about 5 μm, including about: 2.5, 3, 3.5, 4, and 4.5 μm. It will be appreciated that, in embodiments wherein device 1000 comprises a deagglomerator, the preceding values refer to particle size after dispersion into the flow of gas and/or after passing through the deagglomerator.

Examples of active agents which may be delivered according to the present invention include beta-2-agonists, steroids such as glucocorticosteroids (preferably anti-inflammatories), anti-cholinergics, leukotriene antagonists, leukotriene synthesis inhibitors, pain relief drugs generally, such as analgesics and anti-inflammatories (including both steroidal and non-steroidal anti-inflammatories), cardiovascular agents such as cardiac glycosides, respiratory drugs, anti-asthma agents, bronchodilators, anti-cancer agents, alkaloids (e.g. ergot alkaloids) or triptans such as can be used in the treatment of migraine, drugs (for instance sulphonylureas) useful in the treatment of diabetes type I and II and related disorders, sleep inducing drugs including sedatives and hypnotics, psychic energizers, appetite suppressants, anti-arthritics, anti-malarials, anti-epileptics, anti-thrombotics, anti-hypertensives, anti-arrhythmics, anti-oxidants, anti-depressants, anti-psychotics, auxiolytics, anti-convulsants, anti-emetics, anti-infectives, anti-histamines, anti-fungal and anti-viral agents, drugs for the treatment of neurological disorders such as Parkinson's disease (dopamine antagonists), drugs for the treatment of alcoholism and other forms of addiction, drugs such as vasodilators for use in the treatment of erectile dysfunction, muscle relaxants, muscle contractants, opioids, stimulants, tranquilizers, antibiotics such as macrolides, aminoglycosides, fluoroquinolones and beta-lactams, vaccines, cytokines, growth factors, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents and mixtures of the above (for example the asthma combination treatment containing both steroid and beta-agonist).

The active agent may fall into one of a number of structural classes, including but not limited to small molecules (including insoluble small molecules), peptides, polypeptides, proteins, polysaccharides, steroids, nucleotides, oligonucleotides, polynucleotides, fats, electrolytes, and the like. Specific examples include the beta-2-agonists salbutamol (e.g. salbutamol sulphate) and salmeterol (e.g. salmeterolxinafoate), the steroids budesonide and fluticasone (e.g. fluticasone propionate), the cardiac glycoside digoxin, the alkaloid anti-migraine drug dihydroergotaminemesylate and other alkaloid ergotamines, the alkaloid bromocriptine used in the treatment of Parkinson's disease, sumatriptan, rizatriptan, naratriptan, frovatriptan, almotriptan, zolmatriptan, morphine and the morphine analogue fentanyl (e.g. fentanyl citrate), glibenclamide (a sulphonyl urea), benzodiazepines such as valium, triazolam, alprazolam, midazolam and clonazepam (typically used as hypnotics, for example to treat insomnia or panic attacks), the anti-psychotic agent risperidone, apomorphine for use in the treatment of erectile dysfunction, the anti-infective amphotericin B, the antibiotics tobramycin, ciprofloxacin and moxifloxacin, nicotine, testosterone, the anti-cholenergic bronchodilator ipratropium bromide, the bronchodilator formoterol, monoclonal antibodies and the proteins LHRH, insulin, human growth hormone, calcitonin, interferon (e.g. beta- or gamma-interferon), EPO and Factor VIII, as well as in each case pharmaceutically acceptable salts, esters, analogues and derivatives (for instance prodrug forms) thereof.

Additional examples of potentially suitable active agents include but are not limited to asparaginase, amdoxovir (DAPD), antide, becaplermin, calcitonins, cyanovirin, denileukindiftitox, erythropoietin (EPO), EPO agonists, domase alpha, erythropoiesis stimulating protein (NESP), coagulation factors such as Factor VIIa, Factor VIII, Factor IX, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones, growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau; interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor, lactoferrin and lactoferrin fragments, luteinizing hormone releasing hormone (LHRH), insulin, pro-insulin, insulin analogues, amylin, C-peptide, somatostatin, somatostatin analogs including octreotide, vasopressin, follicle stimulating hormone (FSH), influenza vaccine, insulin-like growth factor (IGF), insulinotropin, macrophage colony stimulating factor (M-CSF), plasminogen activators such as alteplase, urokinase, reteplase, streptokinase, pamiteplase, lanoteplase, and tenecteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1 endothelial growth factors, parathyroid hormone (PTH), glucagon-like peptide, somatotropin, thymosin alpha 1, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyribonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, afeliomomab, basiliximab, daclizumab, infliximab, ibritumomabtiuexetan, mitumomab, muromonab-CD3, iodine 131 tositumomab conjugate, olizumab, rituximab, and trastuzumab (herceptin), amifostine, amiodarone, aminoglutethimide, amsacrine, anagrelide, anastrozole, asparaginase, anthracyclines, bexarotene, bicalutamide, bleomycin, buserelin, busulfan, cabergoline, capecitabine, carboplatin, carmustine, chlorambucin, cisplatin, cladribine, clodronate, cyclophosphamide, cyproterone, cytarabine, camptothecins, 13-cis retinoic acid, all transretinoic acid; dacarbazine, dactinomycin, daunorubicin, dexamethasone, diclofenac, diethylstilbestrol, docetaxel, doxorubicin, epirubicin, estramustine, etoposide, exemestane, fexofenadine, fludarabine, fludrocortisone, fluorouracil, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lomustine, mechlorethamine, medroxyprogesterone, megestrol, melphalan, mercaptopurine, methotrexate, metoclopramide, mitomycin, mitotane, mitoxantrone, naloxone, nicotine, nilutamide, octreotide, oxaliplatin, pamidronate, pentostatin, pilcamycin, porfimer, prednisone, procarbazine, prochlorperazine, ondansetron, raltitrexed, sirolimus, streptozocin, tacrolimus, tamoxifen, temozolomide, teniposide, testosterone, tetrahydrocannabinol, thalidomide, thioguanine, thiotepa, topotecan, tretinoin, valrubicin, vinblastine; vincristine, vindesine, vinorelbine, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicillinase-sensitive agents like penicillin G, penicillin V; penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidineisethiouate, albuterolsulfate; lidocaine, metaproterenolsulfate, beclomethasonediprepionate, triamcinolone acetamide, budesonide acetonide, fluticasone, ipratropium bromide, flunisolide, cromolyn sodium, and ergotamine tartrate; taxanes such as paclitaxel; SN-38; tyrphostines.

Other agents that may be used include: Linezolid; Treprostinol optionally in combination with a PDE5 Inhibitor; Oxyntomodulin; and Palonosetron optionally in combination with a, preferably high potency, NK1 antagonist.

It will be understood that the above exemplary active agents encompass, as applicable, analogues, agonists, antagonists, inhibitors, isomers, and pharmaceutically acceptable salt forms thereof. In regard to peptides and proteins, the invention is intended to encompass synthetic, recombinant, native, glycosylated, non-glycosylated, and biologically active fragments and analogues thereof.

In some typical embodiments, the composition includes one or more active agents selected from adrenaline (epinephrine), glucose, glucagon, naloxone, insulin or the like.

In some typical embodiments the composition includes particulate glucose and/or glucagon for the treatment of hypoglycaemia, diabetes induced coma or the like. In embodiments, the dry powder includes particulate benzodiazepine, phenytoin or anti-seizure medications for the treatment of seizure.

In some typical embodiments, the composition includes one or more agents for inducing an immune response, such as one or more vaccines. In embodiments, the dry powder includes a measles vaccine, for inducing an immune response to, or immunising against, measles. In embodiments, the dry powder includes a Hepatitis B vaccine, for inducing an immune response to, or immunising against. Hepatitis B. In embodiments, the dry powder includes an influenza vaccine, for inducing an immune response to, or immunising against, influenza.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. The invention is intended to embrace all alternatives, modifications, and variations of the present invention that have been discussed herein, and other embodiments that fall within the spirit and scope of the above described invention.

The invention claimed is:

1. A device for delivery of a composition to an airway of a subject, the device having a body defined about a central axis and comprising:
in fluid communication:
a composition receptacle adapted to receive a composition capsule containing the composition;
a dispersion chamber defined by at least one wall which comprises two openings therein, the dispersion chamber located adjacent the composition receptacle; and
a gas outlet,
wherein the two openings are each continuous with a respective flow inlet path each of which is at least partially defined between an outer flow inlet path wall which is continuous with the at least one wall of the dispersion chamber and an inner flow inlet path wall, and each flow inlet path extending between the respective opening and a respective gas inlet allowing gas external to the device to enter the device, each gas inlet having a first end directly in contact with gas external to the device and a second end positioned proximate a respective flow inlet path, the central axis passing through a portion of the first and second ends of each respective gas inlet, the gas inlets form a passage through the body of the device adjacent the dispersion chamber to define an inlet gas axis extending substantially perpendicular to the central axis,
wherein the at least one wall of the dispersion chamber has a distal end adjacent the composition receptacle, defining a first plane, and a proximal end closer to the gas outlet than the distal end and defining a second plane; and each gas inlet is formed in a region of the body of the device overlapping a region formed between the first and second planes,
wherein the flow inlet paths extend in a plane perpendicularly to the central axis between the gas inlets and the two openings in the at least one wall of the dispersion chamber,
wherein the flow inlet paths taper to form at least one point of maximum constriction located adjacent the respective openings in the at least one wall of the dispersion chamber and a cross-sectional area of each flow inlet path decreases on moving from the respective gas inlet in a direction of the respective opening.

2. The device according to claim 1, wherein the flow inlet paths are located only between the first and second planes.

3. The device according to claim 1, wherein an exterior of the body of the device comprises a first wall and a second wall which are spaced apart, one from the other, to create two spaced regions and the gas inlets are formed in the respective spaced region.

4. The device according to claim 1, wherein the flow inlet paths present a slope having an angle of between about 25 to about 60 degrees as measured relative to the dispersion chamber from at least one wall at the point of entry to the dispersion chamber.

5. The device according to claim 1, wherein the gas outlet is co-axial with the central axis.

6. The device according to claim 1, further comprising one or more primers and a cap configured to engage with and displace the one or more primers to pierce the composition capsule upon removal of the cap.

7. The device according to claim 6, wherein the one or more primers each comprise a cam follower and an associated pin or blade, and wherein the cap comprises one or more cams which are located so as to engage with and displace the respective primer to pierce the composition capsule upon removal of the cap.

8. The device according to claim 1, further comprising a deagglomerator located adjacent to the dispersion chamber and between the dispersion chamber and the gas outlet.

9. A device for delivery of a composition to an airway of a subject, the device having a body defined about a central axis and comprising:
in fluid communication:
a composition receptacle adapted to receive a composition capsule containing the composition;
a dispersion chamber defined by at least one wall which comprises two openings therein, the dispersion chamber located adjacent the composition receptacle; and
a gas outlet,
wherein the two openings are each continuous with a respective flow inlet path each of which is at least partially defined between an outer flow inlet path wall which is continuous with the at least one wall of the dispersion chamber and an inner flow inlet path wall, and each flow inlet path extending between the respective opening and a respective gas inlet allowing gas external to the device to enter the device, each gas inlet having a first end directly in contact with gas external to the device and a second end positioned proximate a respective flow inlet path, the central axis passing through a portion of the first and second ends of each respective gas inlet, the gas inlets form a passage through the body of the device adjacent the dispersion chamber to define an inlet gas axis extending substantially perpendicular to the central axis,
wherein the at least one wall of the dispersion chamber has a distal end adjacent the composition receptacle, defining a first plane, and a proximal end closer to the gas outlet than the distal end and defining a second plane and: (i) each gas inlet is formed in a region of the body of the device overlapping a region formed between the first and second planes; and (ii) the flow inlet paths are located only between the first and second planes,
wherein the flow inlet paths taper to form at least one point of maximum constriction located adjacent the respective openings in the at least one wall of the dispersion chamber and a cross-sectional area of each flow inlet path decreases on moving from the respective gas inlet in a direction of the respective opening, and
wherein the gas inlets define a gas inlet axis extending between both gas inlets and each flow inlet path extends at between a 20 to 70 degree angle to the gas inlet axis.

10. The device according to claim 9, wherein an exterior of the body of the device comprises a first wall and a second wall which are spaced apart, one from the other, to create two spaced regions and the gas inlets are formed in the respective spaced region.

11. The device according to claim 9, wherein the flow inlet paths present a slope having an angle of between about 25 to about 60 degrees as measured relative to the dispersion chamber at least one wall at the point of entry to the dispersion chamber.

12. A dry powder inhaler device for delivery of a composition to an airway of a subject, the device having a body defined about a central axis and comprising:
in fluid communication:
a composition receptacle adapted to receive a composition capsule containing the composition;

a dispersion chamber defined by at least one wall which comprises two openings therein, the dispersion chamber located adjacent the composition receptacle; and a gas outlet, wherein the two openings are each continuous with a respective flow inlet path each of which is at least partially defined between an outer flow inlet path wall which is continuous with the at least one wall of the dispersion chamber and an inner flow inlet path wall, and each flow inlet path extending between the respective opening and a respective gas inlet allowing gas external to the device to enter the device, each gas inlet having a first end directly in contact with gas external to the device and a second end positioned proximate a respective flow inlet path, the central axis passing through a portion of the first and second ends of each respective gas inlet, the gas inlets form a passage through the body of the device adjacent the dispersion chamber to define an inlet gas axis extending substantially perpendicular to the central axis, wherein the at least one wall of the dispersion chamber has a distal end adjacent the composition receptacle, defining a first plane, and a proximal end closer to the gas outlet than the distal end and defining a second plane and: (i) each gas inlet is formed in a region of the body of the device overlapping a region formed between the first and second planes; and (ii) the flow inlet paths are located only between the first and second planes, wherein an exterior of the body of the device comprises a first wall and a second wall which are spaced apart, one from the other, to create two spaced regions and the gas inlets are formed in the respective spaced region, wherein the flow inlet paths extend in a plane perpendicularly to the central axis between the gas inlets and the two openings in the at least one wall of the dispersion chamber, wherein the flow inlet paths taper to form at least one point of maximum constriction located adjacent the respective openings in the at least one wall of the dispersion chamber and a cross-sectional area of each flow inlet path decreases on moving from the respective gas inlet in a direction of the respective opening, and wherein the gas inlets define a gas inlet axis extending between both gas inlets and each flow inlet path extends at between a 30 to 50 degree angle to the gas inlet axis.

13. The device according to claim 12, wherein the gas inlets define a gas inlet axis extending between both gas inlets and each flow inlet path extends at between a 34 to 48 degree angle to the gas inlet axis.

14. A dry powder inhaler device for delivery of a composition to an airway of a subject by inhalation, the device having a body defined about a central axis and comprising:

in fluid communication:

a composition receptacle adapted to receive a composition capsule containing the composition;

a dispersion chamber defined by at least one wall which comprises two openings therein, the dispersion chamber located adjacent the composition receptacle; and a gas outlet, wherein:

(i) the two openings are each continuous with a respective flow inlet path each of which is at least partially defined between an outer flow inlet path wall which is continuous with the at least one wall of the dispersion chamber and an inner flow inlet path wall, and each flow inlet path extending between the respective opening and a respective gas inlet allowing gas external to the device to enter the device, each gas inlet having a first end directly in contact with gas external to the device and a second end positioned proximate a respective flow inlet path, the central axis passing through a portion of the first and second ends of each respective gas inlet, the gas inlets form a passage through the body of the device adjacent the dispersion chamber to define an inlet gas axis extending substantially perpendicular to the central axis;

(ii) an exterior of the body of the device comprises a first wall and a second wall which are spaced apart, one from the other, to create two spaced regions and the gas inlets are formed in the respective spaced region;

(iii) the flow inlet paths extend in a plane perpendicularly to the central axis between the gas inlets and the two openings in the at least one wall of the dispersion chamber;

(iv) a cross-sectional area of each flow inlet path decreases on moving from the respective gas inlet in a direction of the respective opening;

(v) the flow inlet paths taper to form at least one point of maximum constriction located adjacent the respective openings in the at least one wall of the dispersion chamber;

(vi) the gas inlets define a gas inlet axis extending between both gas inlets and each flow inlet path extends at between a 30 to 50 degree angle to the gas inlet axis; and (vii) the at least one wall of the dispersion chamber has a distal end adjacent the composition receptacle, defining a first plane, and a proximal end closer to the gas outlet than the distal end and defining a second plane and: (i) each gas inlet is formed in a region of the body of the device overlapping a region formed between the first and second planes; and (ii) the flow inlet paths are located only between the first and second planes; and (viii) the flow inlet paths present a slope having an angle of between about 30 to about 50 degrees as measured relative to the dispersion chamber at least one wall at the point of entry to the dispersion chamber.

15. The device according to claim 14, further comprising one or more primers and a cap configured to engage with and displace the one or more primers to pierce the composition capsule upon removal of the cap.

16. The device according to claim 14, wherein the flow inlet paths present a slope having an angle of between about 30 to about 45 degrees as measured relative to the dispersion chamber at least one wall at the point of entry to the dispersion chamber.

* * * * *